United States Patent
Essiger

(10) Patent No.: US 7,172,422 B1
(45) Date of Patent: Feb. 6, 2007

(54) DEVICE FOR REGENERATING, REPAIRING, AND MODELING HUMAN AND ANIMAL BONE, ESPECIALLY THE JAW AREA FOR DENTAL APPLICATIONS

(75) Inventor: Holger K. Essiger, Speckweg 3, Wedemark (DE) D-30900

(73) Assignee: Holger K. Essiger (DE)

( * ) Notice: Subject to any disclaimer, the term of this patent is extended or adjusted under 35 U.S.C. 154(b) by 0 days.

(21) Appl. No.: 09/394,135

(22) Filed: Sep. 10, 1999

Related U.S. Application Data

(63) Continuation-in-part of application No. 09/113,031, filed on Jul. 9, 1998, now abandoned.

(30) Foreign Application Priority Data

Jul. 9, 1997 (DE) ................................ 197 29 222
Feb. 1, 1998 (DE) ................................ 198 03 628

(51) Int. Cl.
*A61C 8/00* (2006.01)
(52) U.S. Cl. ...................................... 433/173; 433/172
(58) Field of Classification Search ........ 433/172–176, 433/201.1, 213, 214
See application file for complete search history.

(56) References Cited

U.S. PATENT DOCUMENTS

| 4,516,937 | A | * | 5/1985 | Bosker ....................... 433/173 |
| 4,696,290 | A | * | 9/1987 | Steffee ........................ 606/61 |
| 4,767,328 | A | * | 8/1988 | Branemark ............. 433/173 X |
| 4,904,186 | A | * | 2/1990 | Mays ..................... 433/173 X |
| 5,460,526 | A | * | 10/1995 | Bosker ................... 433/172 X |
| 5,527,182 | A | * | 6/1996 | Willoughby ................. 433/172 |
| 5,554,027 | A | * | 9/1996 | Branemark ................. 433/173 |
| 6,096,040 | A | * | 8/2000 | Esser .......................... 606/69 |
| 6,305,938 | B1 | * | 10/2001 | Branemark ................. 433/173 |
| 6,355,038 | B1 | * | 3/2002 | Pisharodi ..................... 606/61 |

* cited by examiner

*Primary Examiner*—Nicholas D. Lucchesi
(74) *Attorney, Agent, or Firm*—Robert W Becker & Associates; Robert W Becker

(57) ABSTRACT

A device for reshaping human or animal bone with bone replacement material includes at least two spaced apart implants and a bar connected to the at least two spaced apart implants and bridging at least one reshaping location. The bar has notches at the longitudinal sides and transverse grooves at the underside. The bar has slotted holes extending in the longitudinal direction of the bar for receiving the implants, respectively, fasteners of the implants.

7 Claims, 2 Drawing Sheets

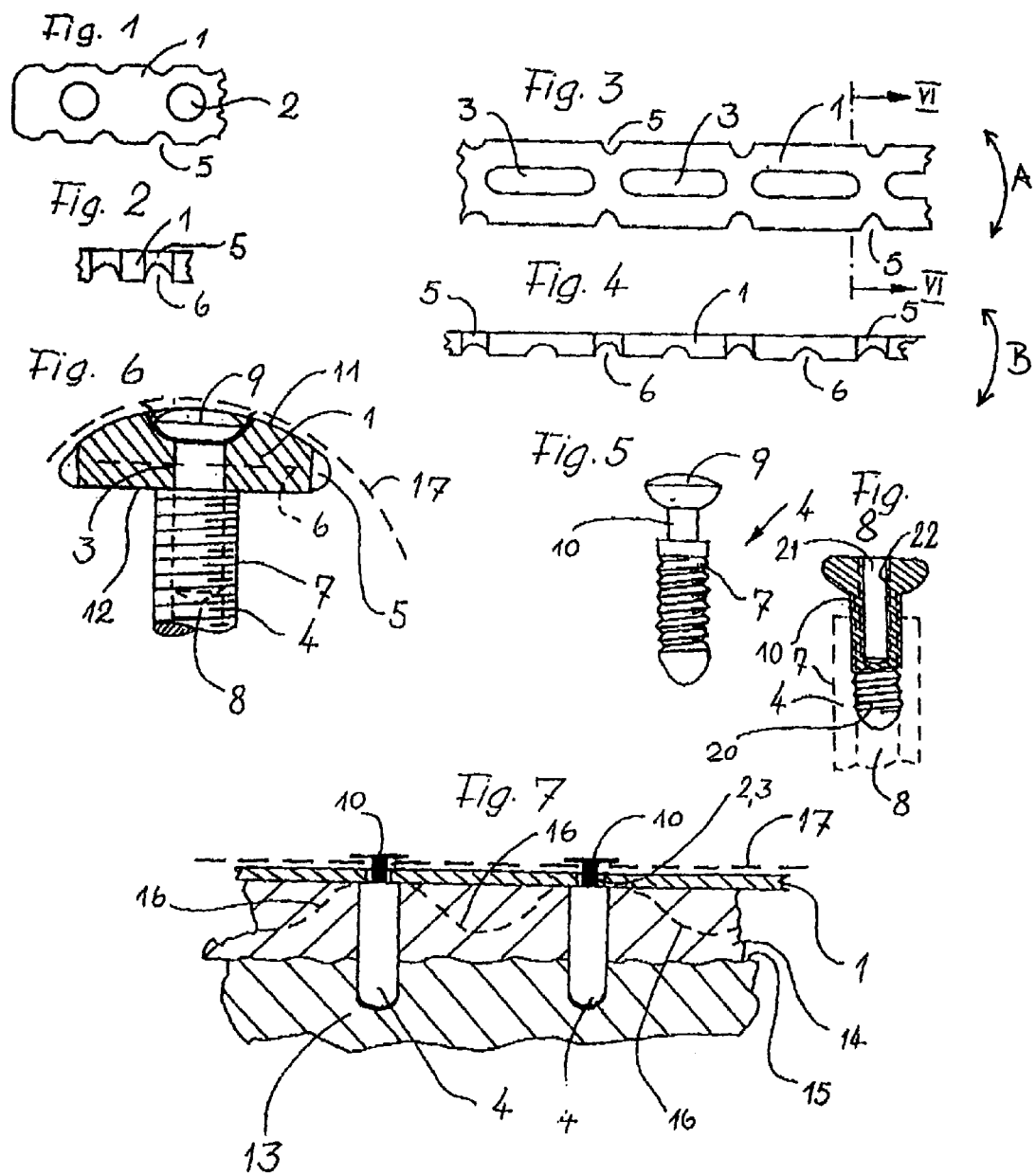

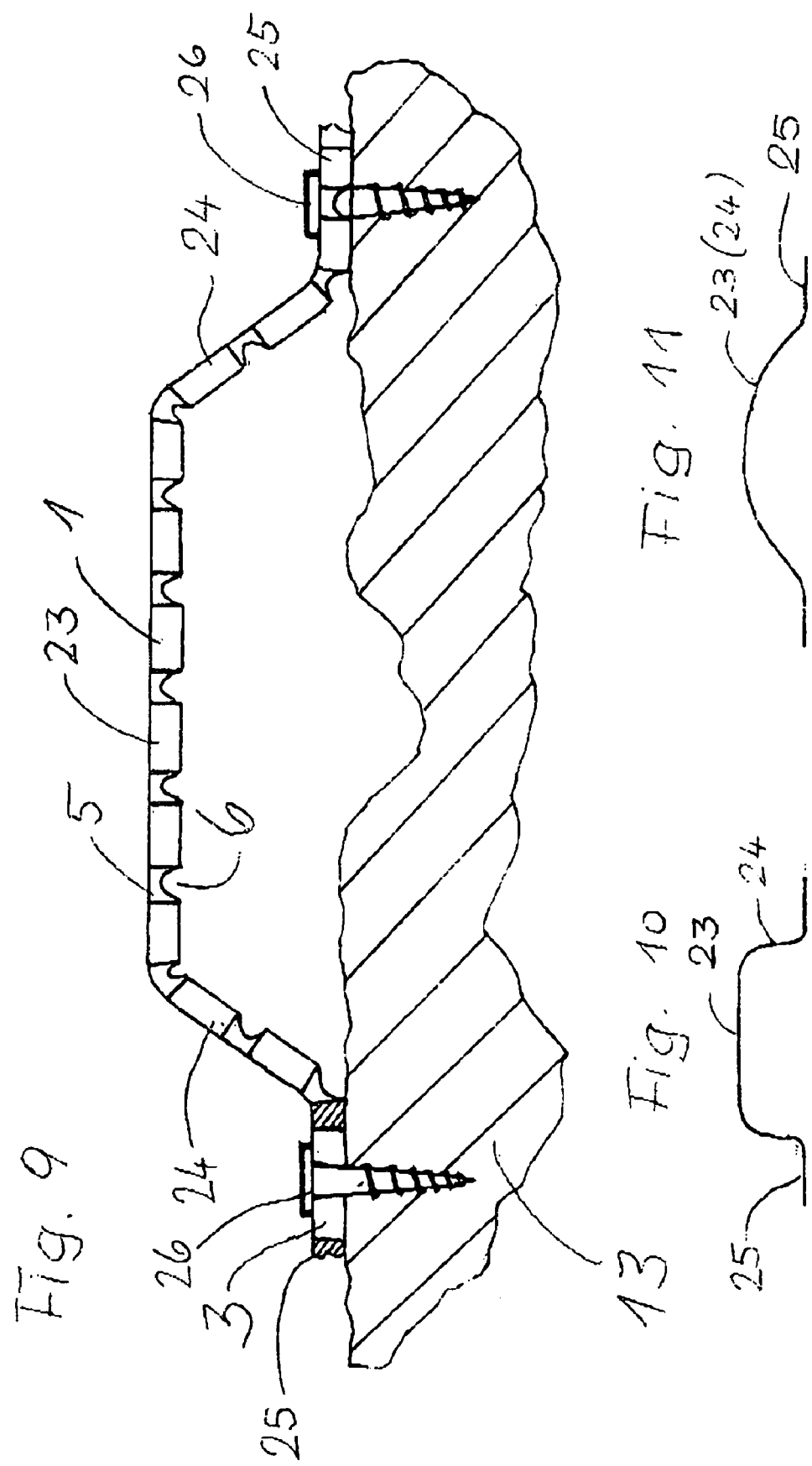

DEVICE FOR REGENERATING, REPAIRING, AND MODELING HUMAN AND ANIMAL BONE, ESPECIALLY THE JAW AREA FOR DENTAL APPLICATIONS

This application is a continuation-in-part of application Ser. No. 09/113,031 filed Jul. 9, 1998, now abandoned.

BACKGROUND OF THE INVENTION

The present inventions relates to a device for reshaping (regenerating, reconstructing, repairing, and modeling) human and animal bones with any type of bone material, for example, synthetic bone material and bone modeling proteins (BMP), especially in the jaw area for dental applications. Accordingly, the device can be used in all areas of a human or animal skeleton, for repairing and modeling bone portions, for example, also complicated fractures with defective bone areas, whereby the device is not limited to a certain bone shape.

The invention is based on the knowledge that the different materials employed for the regeneration of bone material, for example, a patient's own ground bone material and/or, for example, Bio-Oss (trademark), is comparatively pressure-sensitive and can thus atrophy or be resorbed during the healing and building phase. Accordingly, in the known regeneration methods, for example, of the human jaw, atrophies and constrictions as well as bone loss cannot be avoided. The desired effect of a regeneration or reconstruction as complete as possible, especially in the vertical dimension, can thus practically not be achieved.

The aforementioned and other known substances which serve for regenerating and reconstructing bone, including bone blocks, are in the following referred to as bone replacement materials.

The invention has the object to avoid the aforementioned disadvantages of atrophy, i.e., constrictions between the implant and all other bone deposits and repair locations as well as respective contour changes.

SUMMARY OF THE INVENTION

The present invention suggests a device which is characterized by a bending-resistant bar or strip for bridging reshaping locations, i.e., regenerating, repair, and modeling locations, at the bone and which can be supported by two spaced apart implants. This bar or strip receives pressure forces and thus reduces substantially a pressure loading of the bone replacement materials. Furthermore, the bar distributes locally occurring forces onto larger areas in order to thus reduce specific pressure forces. At the same time, the bar also protects and stabilizes the correlated implants. Also, the bar has the advantage to secure and optionally fasten the membranes which are employed during such regeneration processes, for example, for retaining connective tissue. The membranes can be fastened by guiding the membrane across the bar so that the membrane is supported on the bar.

Expediently, the bar has two or more penetrations distributed over its length, for example, in the form of slotted holes, through which fasteners, for example, pins or screws, are guided which are secured or screwed into the implant. The slotted holes have the advantage that the bar can be secured at implants having non-uniform spacing between them.

While known implants for the dental jaw area are provided with roughened surfaces, depressions, or penetrations, the present invention suggests pin-shaped, for example, cylindrical, implants which are polished at their exterior surface and are thus so smooth that in the implanted state they can be rotated, when applying a force, about its longitudinal axis even after having been implanted for an extended time period. Also, it is especially advantageous in this context when the implants are provided with an outer thread. These implants are height-adjustable by rotation and, in the case of bone reconstruction to be carried out stepwise, can be adjusted with respect to their relative vertical position by sequential steps of approximately 4 mm after an initial build-up phase of approximately nine months. The bar connected thereto is then also raised accordingly.

After regeneration, the implants can be removed or support elements for dental replacements or prostheses (crowns, bridges etc.) or other utilitarian elements can be provided.

BRIEF DESCRIPTION OF THE DRAWINGS

The object and advantages of the present invention will appear more clearly from the following specification in conjunction with the accompanying drawings, in which:

FIG. 1 shows a plan view onto a longitudinal section of a bar which is suitable for regeneration of the jaw bone;

FIG. 2 shows the bar section according to FIG. 1 in a side view;

FIG. 3 shows a bar in a plan view which is slightly differently embodied as the one shown in FIG. 1;

FIG. 4 shows the bar section according to FIG. 3 in a side view;

FIG. 5 shows an implant in an end view which can be used in connection with the bar of FIGS. 1–4;

FIG. 6 shows a section along the line VI—VI of FIG. 3 together with an implant according to FIG. 5;

FIG. 7 shows a schematically represented longitudinal section of the regeneration area of a jaw bone to be reconstructed;

FIG. 8 shows a part sectional view of the fastening element for a bar;

FIG. 9 shows a schematically represented longitudinal section of the regeneration area of a jaw bone to be reconstructed with a bar according to FIGS. 3 and 4 bent into a bridge structure;

FIG. 10 illustrates schematically a bar according to FIGS. 3 and 4 in a differently bent bridge structure; and FIG. 11 illustrates schematically a bar according to FIGS. 3 and 4 in a differently bent bridge structure; and

DESCRIPTION OF PREFERRED EMBODIMENTS

The present invention will now be described in detail with the aid of several specific embodiments utilizing FIGS. 1 through 11.

The bar 1, which is manufactured of titanium or any other suitable material, has a substantially flat design of great length extension and, when viewed in cross-section, has centrally arranged penetrations in the form of round holes 2, preferably however slotted holes 3 (see FIG. 3) extending in the longitudinal direction of the bar and distributed over its length. The slotted holes 3 provide for an improved adaptation to imprecisely positioned implants 4, i.e., the bar 1 can be easily positioned even if the position of the implants 4 deviates from the preset, desired location.

The bar or strip 1 has at both edges recesses 5 and at the underside it is provided with transverse grooves 6. Such reductions 5, 6 in the cross-sectional shape allow for cutting to length and deformation of the bar 1 which is produced as a member of great length. The transverse grooves 6 allow easy cutting to length of the bar 1 as well as bending of the bar 1 out of the plane of the bar 1 (indicated by arrow B in FIG. 4). The notches 5 allow bending deformation in the plane of the bar 1 (indicated by arrow A in FIG. 3) in order to adapt the bar 1 to the jaw curvature of the patient. The notches 5 and the grooves 6 are thus predetermined bending locations. These predetermined bending locations allow a reshaping of the bar 1 according to the patient's specification, but also allow bending of the bar 1 during oral surgery and during implantation in order to properly adjust the fit of the bar 1 to the patient's jaw. The arrangement of the grooves 6 at the bottom side of the bar 1 is advantageous because the upper side is thus relatively smooth and will not bother the patient.

The notches 5 and the transverse grooves 6 can also be designed as rated break points so that a required length of the bar 1 can be simply broken off and no cutting tools are required. It is also possible to provide rated break points in addition to the notches 5 and the transverse grooves 6.

The pin-shaped implants are comprised of, for example, titanium or any other suitable material. Within the entire central shaft area an outer thread 7 is provided. Otherwise, they are embodied so as to be very smooth or polished in order to be able to rotate the implant 4 in its operative position, i.e., when implanted, about its longitudinal axis so that the implant 4 can be threaded in and out of the bone, as needed. For this purpose, the implant 4 can be designed at the upper end or head portion such that it has a hexagon socket head in order to facilitate rotation. The implant 4 has also a longitudinal receiving bore 8 embodied as a blind bore open at the upper end. The bore 8 is provided for receiving a fastener 10 with lens-shaped head 9, for example, shaped like a screw or a pin. The fastener 10, after removal of the bar 1, may optionally provide in the area of the implant 4 a cover for the implant 4, respectively, a closure element.

The diameter of the bores 2, respectively, the width of the slotted holes 3 is designed to match the diameter of the fastener 10, while the diameter of the implant 4 is slightly greater than the aforementioned diameter, respectively, the aforementioned width. Accordingly, the bar 1, after having been cut to length, can be placed according to FIG. 6 onto the implants 4 and can be secured thereat with the aid of the fasteners 10. Since the bores 2, respectively, slotted holes 3 widen at the upper side of the bar 1, the lens-shaped head 9 according to FIG. 6 is countersunk in order to prevent it from projecting.

As can be seen in FIG. 6, the upper side 11 of the bar is curved, respectively, convexly designed in order to prevent in its operative position perforations of the soft tissue, respectively, of the synthetic material possibly positioned there. The underside 22 of the bar 1 is designed substantially planar, but optionally can also be concave.

In FIG. 7, the bone to be regenerated or reshaped is indicated by reference numeral 13 and the reconstructed layer is indicated by reference numeral 14. The initial bone contour is indicated by reference numeral 15.

When it is assumed that a plurality of implants 4 is arranged in the reconstructed area 14, but without the bar 1 and without the special design of the implants according to FIG. 5, and when employing a conventional free comb-shaped bone transplant, the resulting atrophy produces a contour according to the dashed line 16. When, instead, according to FIG. 7, a bar 1 is provided at a spacing to the area to be reconstructed, pressure loading of the reconstructed layer 14 is avoided and the reconstructed layer remains intact. The bar 1 is spaced from the contour 15 by the implants 4 and not only bridges the reconstructed material between the implants 4, but also stabilizes the implants 4.

The presence of the bar 1 also allows possibilities for other applications in that a membrane 17, especially for protecting the reconstructed layer 14 and for separating and retaining the connective tissue, can be provided. The membrane 17 covers the bar 1 and can be attached thereto by the lens-shaped head 9 whereby the fasteners 10 penetrate the membrane 17 and clamp the membrane 17 between the bar 1 and the lens-shaped head 9.

After completion of the desired reshaping (regeneration and/or apposition), the membrane 17 and the bar 1 are removed.

It should be noted that the notches 5 must be positioned remote from the slotted holes 3, as can be seen in FIG. 3, in order to prevent a width reduction (denting) of the slotted holes 3 during deformation of the straight bar 1 into the substantially U-shaped jaw-shape, respectively, a curved shape of another bone.

It should also be noted that the represented mechanical connection between the bar 1 and the implant 4 is advantageous, that, however, other connecting means can be used. It is important in this context that the implanted bar 1 in the area of its upper side 11 has a curvature, i.e., is rounded and thus prevents perforations of the mucus membranes or other tissues or materials, and thus also of the membrane 17.

It should further be noted that the invention includes such bars 1 which already during manufacture (instead of being produced as a straight endless bar to be cut to length) have been shaped to the typical design of the bone to be treated, for example, for a jaw bone the bar has a substantially U-shaped contour in a top view.

Even though the disclosed invention, respectively, the inventive bar is primarily designed for bone reconstruction or regeneration of the human jaw, it can also be used at any other location within the skeleton of a human or animal, for example, for reshaping and reconstructing fractures.

After treatment the bar 1 is removed. However, it is within the gist of the present invention to leave the bar 1 at the treatment location, if so desired.

The embodiment of FIG. 8 has a special feature in comparison to the one of FIG. 5. In FIG. 8 there is also shown a fastener 10 for the bar 1 with outer thread 20, but the fastener 10 has an upwardly open blind bore 21 with inner thread 22, penetrating the head and a portion of the shaft of the fastener. The blind bore 21, after mounting of the bar 1 and providing penetrations in optionally present covers (mucous membrane), receives preferably threadable fastening devices for prostheses, bridges or other dental chewing aids and/or cosmetic devices and/or reconstructive devices positioned external to or above the skin. The attachment may be temporary or permanent. This additional attachment function of the fastener 10 has the advantage that, for example, in reconstructive oral (jaw) surgery the patient who is generally without teeth will be able to chew again. In any case, it is at least possible to realize cosmetic purposes. The fastening devices, which are not disclosed in any detail, can be of any desired kind and, for example, may be conical pins. A threaded embodiment is not a requirement.

FIG. 9 shows a shaped bar 1 that is bent into a bridge structure with a raised bridge portion 23, 24 and fastened to the jaw by fastening means, such as screws 26 or implants (4) or bone nails, extending through penetrations provided at the end portions 25 of the shaped bar 1 resting on the bone 13. In the shown embodiment, the fastening means are screws 26 penetrating a penetration in the form of a respective slotted hole 3. The spacing to the bone 13 is thus provided by the slanted lateral portions 24 of the raised bridge portion of the bent bar 1, whereby the central area 23 of the raised bridge portion of the bar 1 extends substantially parallel to the bone 13. In the shown embodiment, the portions 23, 24, 25 are straight. However, it is also possible to curve each portion 23, 24, 25 slightly or to angle the individual portions 23, 24, 25. The bending locations are the grooves 6 at the underside of the bar 1.

FIG. 9 shows a bar according to FIGS. 3, 4. However, the bar 1 can also be designed without notches, grooves or slotted holes and can be preshaped into the desired bridge structure. Since the raised bridge portion must not be connected to implants 4, slotted holes 3 are not required.

FIGS. 10 and 11 show variations of the embodiment of FIG. 9. FIG. 10 shows a reduced angle between the portions 25 and 24, respectively, 24 and 23 in comparison to FIG. 9. FIG. 11 shows a substantially continuous bending of the bar from one end portion 25 to the other end portion 25 so that the lateral portions 24 and the central portion 23 are no longer discernable.

The specification incorporates by reference the disclosure of German priority document 197 29 222.4 of 9 Jul. 1997 and 198 03 628.0 of 1 Feb. 1998.

The present invention is, of course, in no way restricted to the specific disclosure of the specification and drawings, but also encompasses any modifications within the scope of the appended claims.

What is claimed is:

1. A bending-resistant bar for reshaping human or animal bone with bone replacement material by bridging with said bar at least one reshaping location; said bar having a flat cross-section; said bar comprising at least two slotted holes extending in a longitudinal direction of said bar and distributed evenly along the length of said bar; said bar having longitudinal edges with notches; said bar having an underside having transverse grooves extending perpendicularly to said longitudinal direction over the entire width of said bar; wherein said notches and said transverse grooves provide predetermined bending locations for said bar.

2. A bar according to claim 1, wherein said bar has a convex top side.

3. A bar according to claim 1, wherein said notches and said transverse grooves are rated break points.

4. A bar according to claim 1, wherein said bar has rated break points.

5. A bar according to claim 1, wherein said notches are positioned between said slotted holes.

6. A bar according to claim 1, wherein said transverse grooves open into said notches.

7. A method for reshaping human or animal bone with bone replacement material; said method comprising the steps of:

implanting implants into the bone;

mounting a bar according to claim 1 on a support surface of said implants to bridge at least one reshaping location, wherein said implants have a smooth mantle surface so that said implants can be rotated about a longitudinal axis when implanted in order to allow height adjustment of said implants relative to the bone;

height-adjusting the bar relative to the bone during reshaping by adjusting the implants as reshaping progresses;

removing the bar and optionally the implants after completion of reshaping.

* * * * *